United States Patent
Törmälä et al.

(10) Patent No.: US 6,319,264 B1
(45) Date of Patent: *Nov. 20, 2001

(54) HERNIA MESH

(75) Inventors: Pertti Törmälä; Senja Paasimaa, both of Tampere; Teuvo Antikainen, Jyväskylä, all of (FI)

(73) Assignee: Bionx Implants Oy, Tampere (FI)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/054,672

(22) Filed: Apr. 3, 1998

(51) Int. Cl.⁷ .................................................. A61B 17/08
(52) U.S. Cl. .............................................................. 606/151
(58) Field of Search ...................... 606/151–200, 606/213, 110, 112, 111; 602/43, 44; 623/11; 604/304–308

(56) References Cited

U.S. PATENT DOCUMENTS

| | | | |
|---|---|---|---|
| 4,841,962 | * | 6/1989 | Berg et al. ............................ 606/151 |
| 4,997,425 | * | 3/1991 | Shioya et al. ......................... 604/304 |
| 5,007,916 | * | 4/1991 | Linksy et al. ........................ 606/151 |
| 5,508,036 | * | 4/1996 | Bakker et al. ........................ 424/424 |
| 5,634,931 | * | 6/1997 | Kugel .................................... 606/151 |
| 5,686,090 | | 11/1997 | Schilder et al. . |

FOREIGN PATENT DOCUMENTS

| | | |
|---|---|---|
| 3619197 | 12/1987 | (DE) . |
| 0 797 962 | 10/1997 | (EP) . |
| 2 222 954 | 3/1990 | (GB) . |
| WO 96/31157 | 10/1996 | (WO) . |
| WO 96/41596 | 12/1996 | (WO) . |

* cited by examiner

*Primary Examiner*—Olik Chaudhuri
*Assistant Examiner*—Vikki Hoa B. Trinh
(74) *Attorney, Agent, or Firm*—Kenyon & Kenyon

(57) ABSTRACT

According to the present invention, a flexible, fibrous hernia mesh is provided, which is intended to be implanted to close hernia defects. The mesh has at least two functional components or layers: (1) a rapidly degradable first layer and (2) a more slowly degradable (with respect to the first layer) second layer. Using the fibrous mesh of this invention, the hernia defect can be closed so that a) the second layer supports the area until the scar tissue is strong enough (around 6 months), to prevent recurrent hernia formation, b) while the more rapid degradation of the first layer induces scar tissue formation due to inflammatory reaction, and c) the second layer isolates the first layer from the abdominal cavity, preventing tissue to tissue adhesion onto the intestines. The mesh is placed on the uncovered fascia area with its more rapidly absorbable side (the first layer) towards the fascia.

13 Claims, 2 Drawing Sheets

HERNIA MESH

FIELD OF THE INVENTION

The present invention relates to a biologically active hernia mesh, and methods of its manufacture.

BACKGROUND OF THE INVENTION

Traditionally, a hernia bulging through any region of the abdominal wall would be repaired by an open hernioplasty and based on a method where the hernia defect becomes closed and reinforced by adjacent tissues. In cases of very large or recurrent hernias, meshes of some nonabsorbable synthetic material have been used for repair. During a period of 3 to 6 months following the hernia operation, the repaired site gradually gathers scar tissue which builds up to strengthen the region.

Recurrent hernias are a common problem in hernia surgery. Even the best reports indicate from 1% to 4% recurrent hernias after primary surgery, and some authors report figures up to 20%. These figures are much lower when a non-absorbable mesh is utilized in the method of repair.

The new trends for hernia repair include mini-invasive techniques, in which the hernia defect is closed by a piece of non-absorbable mesh with minimal tension. The follow-up times thus far are short for such procedures, but it seems that recurrence rates of 1% or below could be expected. Also, the general recovery time has become shorter, and the patients are usually encouraged to begin their normal activities with no restrictions within a week after the operation.

The commercially available meshes used in hernia repair today are typically made of various plastics. They are known to stay biostable and safe at least for the usual follow-up time of 5 to 10 years after implantation. However, many hernia patients are young people with expected lifespans of decades. Nothing is known about the fate of, or tissue reactions possibly awakened by, the relatively massive plastic meshes after implantation and passage of some decades. Permanent surgical implants (metals, plastics, silicone, etc.) have been shown to cause side effects in many patients because of corrosion, wearing, migration, chronic inflammation and risk of infection. When the foreign material is placed near sensitive organs, the risks of these side effects can be severe to the patient's well being. In the case of hernia surgery, the plastic mesh will always become situated into close contact with the sensitive intra-abdominal organs.

Bioabsorbable meshes made of polyglycolic acid and its lactide copolymer (e.g., DEXON™, available from Davis & Geck, USA; and VICRYL™, available from Ethicon, Johnson & Johnson, U.S.A., are also known. Since the 1970's, these same materials have been used in surgery as sutures. No major harm to the tissues has been generally reported from use of these materials, and these materials also induce fibrogenesis and scar formation to some extent. Unfortunately, sutures and meshes manufactured of polyglycolic acid or its lactide copolymers (with around 10 mol-% of lactide units) tend to lose their strength within about 1 month after implantation, in which time the hernia site would not have enough time to heal and form scar tissue to resist pressure.

SUMMARY OF THE INVENTION

According to the present invention, a flexible, fibrous hernia mesh is provided, which is intended to be implanted to close hernia defects. The mesh has at least two functional components or layers: (1) a rapidly degradable first layer and (2) a more slowly degradable (with respect to the first layer) second layer. Using the fibrous mesh of this invention, the hernia defect can be closed so that a) the second layer supports the area until the scar tissue is strong enough (around 6 months), to prevent recurrent hernia formation, b) while the more rapid degradation of the first layer induces scar tissue formation due to inflammatory reaction, and c) the second layer isolates the first layer from the abdominal cavity, preventing tissue to tissue adhesion onto the intestines. The mesh is placed on the uncovered fascia area with its more rapidly absorbable side (the first layer) towards the fascia.

DETAILED DESCRIPTION OF THE EMBODIMENTS

Figure 1:
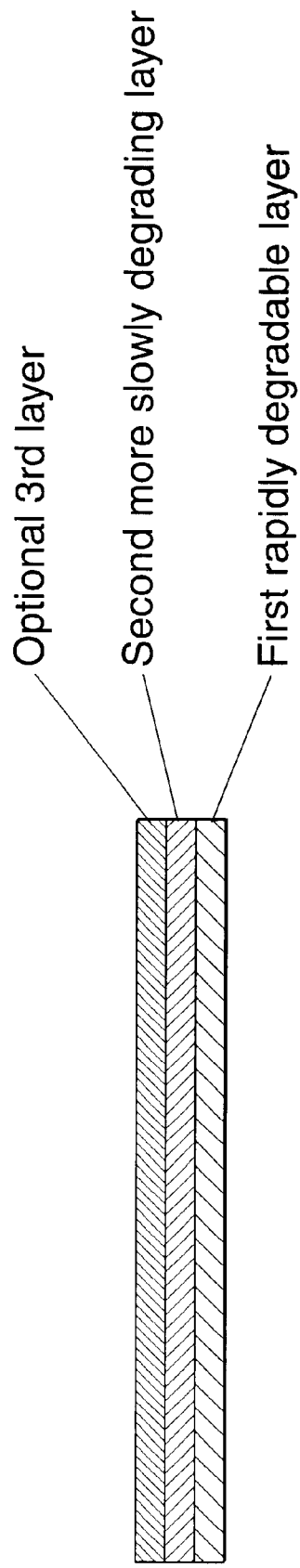
FIG. 1 is a plan view of an embodiment of the present invention.

The present invention relates to an implant, for hernia defect closure, for supporting the formation of scar tissue after implantation and for preventing tissue to tissue adhesion at the same time in the hernioplasty.

In this invention, it has been found out that using a porous, flexible, and fibrous mesh having at least two layers: (1) a more rapidly degradable first layer and (2) a more slowly degradable (with respect to the first layer) second layer, the above mentioned disadvantages of the prior art implants can be largely reduced or avoided, and the methods used for hemioplasty can be improved, particularly to enhance the formation of scar tissue and to avoid any possible long term foreign-body reactions. The hernia mesh of this invention is made from bioabsorbable polymers, copolymers, polymer blends or by combining various bioabsorbable polymer parts.

Using the fibrous mesh of this invention, the hernia defect can be closed so that a) the more slowly degrading (with respect to the first layer) second layer supports the hernia area until the scar tissue is strong enough to prevent recurrent hernia formation (appr. 6 months), b) scar tissue formation is enhanced due to the inflammatory reaction caused by the more rapid degradation of the first layer, and c) tissue to tissue adhesion onto the intestines is prevented. The mesh of the invention is placed on the uncovered fascia area with its more quickly absorbable side towards the fascia. The mesh is fixed with bioabsorbable sutures or clips.

The mesh of the invention when implanted, for example, through a laparoscope, will typically induce strong fibrotic scar tissue formation on the more rapidly degrading first layer of the mesh soon after the operation, due to the porous structure and quick degradation of the first layer. The functions of the second layer are to support the hernia area until the scar tissue is strong enough to resist pressure and to prevent tissue to tissue adhesion onto the intestines. To further improve the tissue to tissue adhesion preventing effect of the mesh, a third layer, a film, can be included as part of the structure of the mesh. The third layer prevents inflammatory agents, which could cause tissue to tissue adhesion, from moving from the hernia area through the mesh and onto the surrounding tissues.

The mesh of the invention acts as a temporary support until the connective scar tissue has strengthened enough and can replace the mesh, when the second layer finally degrades. At that point, the hernia defect closure is then finally formed entirely of the patient's own tissue, following absorption of the whole synthetic mesh. Compared to the so-called biostable meshes, no wear debris will come loose from the bioabsorbable material of the present invention on a long term (e.g., 5 years after operation or later) basis, thereby eliminating risks for long term foreign-body complications or chronic inflammatory reactions.

The mesh according to this invention can be produced of fibers made of bioabsorbable polymer, copolymer, polymer blend or polymer composite, or by combining different bioabsorbable polymer parts. In medical, technical and patent literature there have been presented many polymers, which can be used as a raw material for the fibers of the hernia mesh of this invention. There are, for example, bioabsorbable aliphatic polyesters. polyanhydrides, poly (ortho esters) polymers, which are presented, for example, in FI Pat. Apl 952884 and PCT application PCT/FI96/00351 "Nivelproteesi", the disclosures of which are incorporated herein by reference.

The first layer of the mesh according to this invention is porous, with the optimal pore size being between 50 $\mu$m–1000 $\mu$m. Utilizing this optimal pore size enables the connective tissue cells to grow into the porosity of the mesh after implantation, and strengthens formation of the scar tissue.

The second layer of the mesh according to this invention can be dense or porous, or a combination of both. If the second layer is porous, the optimal pore size is around 0.1 mm to 2.0 mm, in order to maximize the supporting effect of the second layer. However, the second layer is also soft and flexible, in order that the operation can still be accomplished through a laparoscope.

Figure 2:
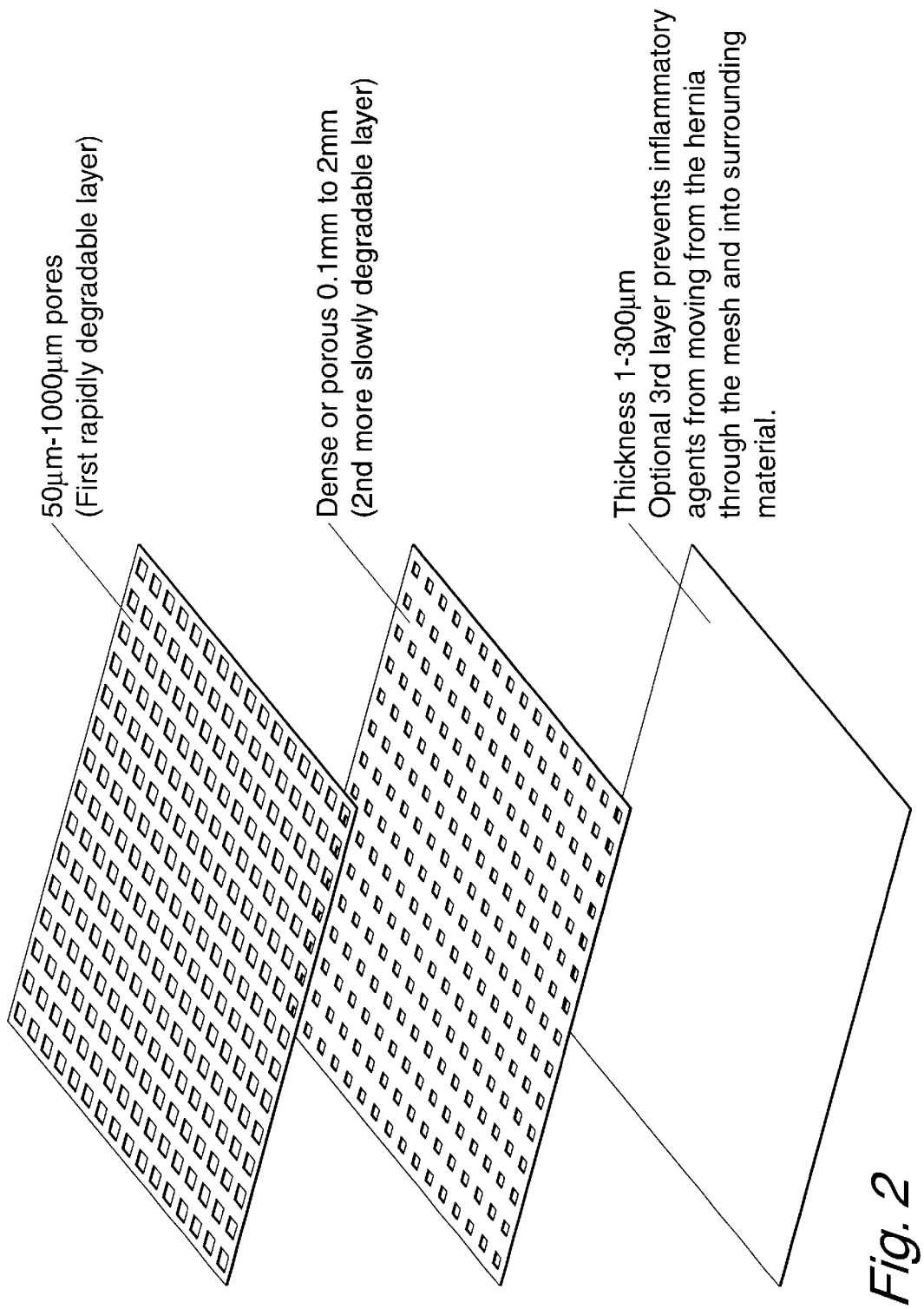
FIG. 2 is an exploded view of an embodiment of the present invention.

The optional third layer of the mesh according to this invention is a dense, thin, bioabsorbable film, which prevents agents that could cause tissue to tissue adhesion from moving from the hernia area through the mesh and onto the surrounding tissue, during the first weeks after the operation. The third layer film also acts as a support layer immediately after the operation. The thickness of the bioabsorbable film is optimally between 1–300 $\mu$m. The third layer is also soft and flexible in order that the operation through a laparoscope is still possible. FIGS. 1 and 2 illustrate an embodiment of the present invention composed of three bioabsorbable layers.

A porous structure is most easily imbued in the mesh of this invention by making the mesh from fibers and using known textile processing methods, for example, knitting, weaving and non-woven manufacturing methods. Also, any other processing methods that result in porous structures can be used to make the mesh of this invention.

Different drugs and/or growth factors can be added into the mesh structure of the invention, to improve the functionality of the implant. Angiogenetic growth factors can be used to accelerate the growth of connective tissue. Also, for example, cyclosporine can be used in the structure to prevent, more effectively, tissue to tissue adhesion of the mesh onto the intestines The functionality of this invention is further described in the following non-restrictive examples.

EXAMPLE 1

The hernia mesh was made of commercial polyglycolide (PGA) biosbsorbable DEXON MESH™ (available from Davis & Geck, USA) and more slowly degradable poly (L/D lactide), [P (L/D)LA, monomer ratio 96/4, I.V.=6.8 dl/g, producer Purac Biochem, The Netherlands)].

Fibers were melt-spun with a one screw extruder (Axon, Sweden), and the polymer melt (at T=200–270° C.) was pressed through four round die holes having a diameter of 0.4 mm. After cooling to room temperature, the filaments were oriented freely in a two step process at elevated temperature (60–140° C.). The draw ratio was 4–8. The final filament diameter was 50 $\mu$m The filaments were then knitted by using a warp knitting machine, the fabric having a loop size of about 1 mm. The knitted fabric was combined with the DEXON MESH™ by sewing. The dimensions of this fibrous two-layer composite mesh were 25 cm×15 cm. The meshes were sterilized with ethylene oxide gas.

EXAMPLE 2

The hernia mesh was made using two different polymers as raw materials: the copolymer of L lactic acid and and glycolide (P(L/GA), monomer ratio 10/90, i.v. 1.58 dl/g, producer Purac Biochem b.v., The Netherlands) and poly L/D lactide (monomer ratio L/D 96/4, i.v. 6.8 dl/g, producer Purac Biochem b.v., The Netherlands). The fibers were spun as in Example 1. The multifilament yarns were knitted into a form of hybrid fabric having a mesh like structure. The mesh was sterilized with ethylene oxide gas.

EXAMPLE 3

The hernia mesh was made of the commercial bioabsorbable PGA DEXON MESH™, style 4, and copolymer of L-lactic acid and $\epsilon$-caprolactone, P(L-LA/E-CL) available from the Helsinki University of Technology ("HUT"), Finland, having a monomer ratio of 10/90 and $M_w$=260,000 dalton.

Biaxially oriented P(L-LA/E-CL) film having thickness of 20 $\mu$m was made using an extrusion process. The film and the DEXON MESH™ were fixed together by sewing. The final composite mesh had dimensions of 12×10 cm. The meshes were sterilized with ethylene oxide gas.

EXAMPLE 4

Laparoscopic Hernioplasty

The patient was in general anesthesia and laying supine in an 20 degree Trendelenburg's position. The abdominal cavity was penetrated by a needle and insufflated up to 10 mmHg using carbondioxide gas. Three troacars (10/12 mm) are thus placed: the first near the umbilicus and the other two some centimeters below on each side. The hernial sac (peritoneum) was grasped and pulled from the hernial defect. The sac was then opened by beginning the dissection laterally from the inner inguinal canal and advancing medially 3 cm across the edge of the rectus muscle. Thus, the flap of peritoneum was created under which the fascia of transversus abdominis was seen. A tightly rolled 8×10 cm composite mesh according to Example 1 was introduced into the abdominal cavity, unrolled and placed on the uncovered fascia area with its more quickly absorbable (PGA) side towards the fascia. The peritoneal flap was then placed over the mesh and both were fixed onto the underlaying fascia with 5 to 10 titanium staples. Sometimes it is difficult to hide all parts of the mesh, but in case of the absorbable composite mesh this does not matter, because the smooth and slowly resorbable P(L/D)LA fiber surface of the mesh will not give rise to intra-abdominal adhesions or irritation. The operation was terminated by desufflating the abdominal cavity, pulling out the trocars and suturing the three 1 cm wounds.

The patient was encouraged to take part in his normal activities after a sick leave of one week.

The hernial defect is closed by a scar plate within 3 to 6 months, in which time the absorbable mesh composite will gradually lose its strength and consistency. In the end, no permanent foreign material will be left when both fibrous components of the mesh have bioabsorbed in around 3–4 years.

EXAMPLE 5

Lichtenstein's hernioplasty (male patient): The patient lays supine. Some 10 to 20 ml of local anesthetic was applied at the inguinal region. An incision measuring 7 cm was positioned along the inguinal ligament and at the level of pubic symphysis. The roof of the inguinal canal was then incised and the spermatic cord detached from its attachments. This reveals the hernial sac and allows the surgeon to invert it back to the abdominal cavity. The inguinal ligament and the lateral border of the rectus abdominis muscle were then exposed. The absorbable mesh composite (size 7.5 cm×15 cm) according to Example 1 is then sutured to these structures. The mesh should now cover the entire inguinal canal allowing only the funicle to pass through. Care must be taken to place the mesh to face its more slowly resorbable side downwards. The roof of the inguinal canal was then reconstructed using resorbable sutures and the skin was closed by sutures or staples. The patient may leave the hospital after some hours. The usual sick leave time is 1 to 2 weeks, after which all daily activities are allowed. The trauma caused by the dissection and the inflammation aroused by the mesh composite will induce fibroplacia to form a scar which, in 3 to 6 months, will support the bottom of the inguinal canal and prevent recurrent hernia formation. No permanent foreign material is left in the patient.

We claim:

1. A hernia mesh for use in repairing a defect in an abdominal wall or cavity, said mesh comprising:
    a first layer capable of being anchored on the abdominal wall next to the defect, wherein said first layer has a first degradation time and is made from a bioabsorbable polymer, copolymer, polymer blend or polymer composite, wherein said first layer is porous and has a pore size between about 50–1000 $\mu$m and
    a second layer, wherein said second layer is configured such that it is fixed on the first layer and capable of being placed in contact with the abdominal wall or cavity wherein said second layer has a second degradation time that is longer than the first degradation time and the second layer is made from a bioabsorbable polymer, copolymer, polymer blend or polymer composite.

2. The hernia mesh as set forth in claim 1, wherein said first layer has a fibrous structure wherein the fibrous structure is made of a fabric selected from the group consisting of woven fabric, knitted fabric, mesh and non-woven felt, and wherein the fabric comprises filament or staple fibers.

3. The hernia mesh as set forth in claim 2, wherein said second layer has a fibrous structure wherein the fibrous structure is made of a fabric selected from the group consisting of woven fabric, knitted fabric, mesh and non-woven felt, and wherein the fabric comprises filament or staple fibers.

4. A mesh as set forth in claims 3, further comprising a third layer comprising a biodegradable film, said third layer being positioned between the first layer and the second layer.

5. A mesh as set forth in claims 4, wherein the mesh is planar like.

6. A mesh as set forth in claims 5, wherein the mesh is made of biodegradable fibers having fiber diameter of 1–300 $\mu$m.

7. The hernia mesh of claim 1 wherein the second layer is porous and has a pore size between about 0.1 to 2.0 mm.

8. The hernia mesh of claim 1 wherein the second layer is dense.

9. The hernia mesh of claim 1 wherein the mesh further comprises growth factors.

10. The hernia mesh of claim 1 wherein the mesh further comprises angiogenic growth factors.

11. The hernia mesh of claim 1 wherein the mesh further comprises cyclosprine.

12. The hernia mesh of claim 4 wherein the third layer is about 1–300 $\mu$m thick.

13. A hernia mesh for use in repairing a defect in an abdominal wall or cavity, said mesh comprising:
    a first layer capable of being anchored on the abdominal wall next to the defect, wherein said first layer has a first degradation time and is made from bioabsorbable polymer, copolymer, polymer blend or polymer composite, wherein said first layer is porous and has a pore size between about 50–1000 $\mu$m; and
    second layer, wherein said second layer is configured such that it is fixed on the first layer and capable of being placed in contact with the abdominal wall or cavity, wherein said second layer has a second degradation time that is longer than the first degradation time, said second layer is made from bioabsorbable polymer, copolymer, polymer blend or polymer composite, and said second layer being capable of isolating the first layer from the abdominal cavity thus preventing tissue adhesion.

* * * * *